United States Patent [19]

Lindemann et al.

[11] 4,312,813

[45] Jan. 26, 1982

[54] BISQUATERNARY AMMONIUM COMPOUND

[75] Inventors: Martin K. O. Lindemann, Bridgewater; Elvin R. Lukenbach, Somerset, both of N.J.

[73] Assignee: Johnson & Johnson Baby Products Company, New Brunswick, N.J.

[21] Appl. No.: 163,121

[22] Filed: Jun. 26, 1980

[51] Int. Cl.³ ............................................. C09F 5/00
[52] U.S. Cl. .............................. 260/404.5; 260/401; 252/545; 252/546; 252/547; 424/70
[58] Field of Search ............. 260/404.5 Q, 404.5 EO, 260/401

[56] References Cited

U.S. PATENT DOCUMENTS

| | | | |
|---|---|---|---|
| 2,259,650 | 10/1941 | Maxwell | 260/404.5 Q |
| 2,583,772 | 1/1952 | Ganderson | 260/404.5 Q |
| 3,074,815 | 1/1963 | Lee et al. | 260/404.5 Q |
| 3,859,378 | 1/1975 | Hochreuter | 260/404.5 Q |

Primary Examiner—John F. Niebling
Attorney, Agent, or Firm—Steven P. Berman

[57] ABSTRACT

Novel bisquaternary ammonium compounds are described and exhibit utility as components in personal care products.

8 Claims, No Drawings

BISQUATERNARY AMMONIUM COMPOUND

The present invention relates to novel bisquaternary ammonium compounds. More particularly, the present invention relates to novel bisquaternary ammonium compounds of the formula:

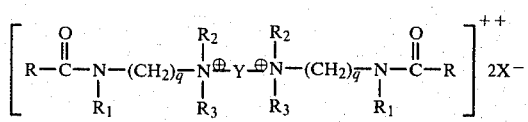

wherein
R is straight or branched chain alkyl, alkenyl, or alkaryl containing from about 8 to 30 carbon atoms and may be optionally interrupted by oxyalkylene groups containing up to a total of 20 carbon atoms;

$R_1$ is hydrogen or alkyl, alkaryl or hydroxyalkyl of from about 1 to 10 carbon atoms;

$R_2$ and $R_3$ are the same or different and are alkyl of from 1 to 6 carbon atoms, hydroxyalkyl of from 1 to 4 carbon atoms or alkaryl of from 1 to 10 carbon atoms;

q is an integer from 2 to 6;

Y is alkylene from about 1 to 10 carbon atoms or oxyalkylene of the formula:

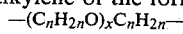

wherein
n is an integer from 2 to 4 and x is an integer from 1 to 16; and

X is an anion such as Cl, Br and the like.

BACKGROUND OF THE INVENTION

Various bisquaternary ammonium compounds are known in the prior art and the compounds disclosed in these patents have been employed as antistatic agents for fibers, U.S. Pat. No. 3,954,633; wetting and washing agents and as dressing for artificial silk, British Pat. No. 474,671; agents for treating clays to prevent swelling, U.S. Pat. No. 3,349,032; agents for imparting water resistant properties to felts, German Pat. No. 2,509,741; when employed as a perchlorate, as photographic sensitizers, U.S. Pat. No. 2,944,902; and as cleansing and nonirritating agents in mild cleansing compositions, U.S. Pat. No. 4,110,263. In this latter patent, the addition of alkyleneoxylated bisquaternary ammonium compounds to anionic and amphoteric detergents reduces the irritant properties of the detergents. None of these patents disclose the specific novel bisquaternary ammonium compounds of the present invention.

SUMMARY OF THE INVENTION

This invention relates to novel bisquaternary ammonium compounds of the formula:

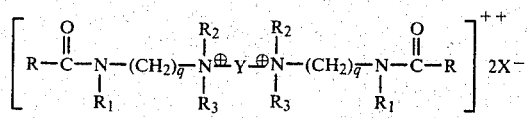

wherein
R, $R_1$, $R_2$, $R_3$, q, Y and X are as defined above.
In these bisquaternary ammonium compounds (which hereinafter may be referred to as "quaternary ammonium compounds" or "bisquaternary ammonium compounds"), the expression "alkyleneoxylated", wherever applicable, refers to the alkyleneoxy bridge, which is joined to the nitrogen through a carbon. In the compounds, the alkylene or alkyleneoxy bridge (Y) is of at least two atoms, i.e., n is 2 and x is 0. The alkylene chain between the oxygens contain from 2 to 4 carbon atoms. Each quaternary nitrogen is substituted with at least one long chain amido group containing an acyl radical of at least 8 carbon atoms. Suitable radicals include octoyl, nonoyl, decenoyl, decoyl, dodecoyl, undecoyl, undecenoyl, tetradecoyl, hexadecoyl, octadecoyl, octadecenoyl, octadecadienoyl, octadetrienoyl, eicosoyl, docosoyl, tricosoyl, hexacosoyl, and the like. The nature of the anion is not critical, however, it should be compatible with the detergent and should be of the type stable in aqueous media. It is usually a water-soluble anion of common inorganic or organic acids, such as ascorbate, bromide, chloride, gluconate, methylsulfate, benzoate, lactate, citrate, salicylate, acetate, formate, N,N-diethyl-p-ammino-benzoate, and the like. Although it may be an anionic detergent group, it is contemplated that the quaternary compound be supplied in a form containing the more simple anions and the detergent type anionic group be supplied in a more conventional form as a commercially available anionic detergent.

The novel bisquaternary ammonium compounds of the present invention may be prepared by the following two step process:

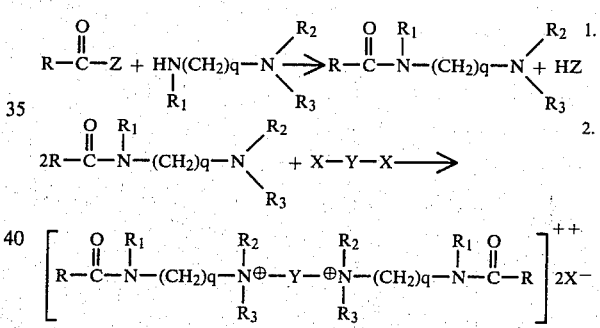

wherein
R, $R_1$, $R_2$, $R_3$, q, X, and Y are as previous defined and wherein Z is selected from the group consisting of OH, Cl and OR' wherein R' is lower alkyl containing from 1 to 4 carbon atoms.

A fatty acid,

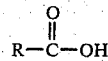

or a reactive fatty acid derivative, i.e., an acid chloride

or ester

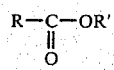

is reacted with a diamine containing one tertiary amine function, i.e., dimethylaminopropylamine or N,N-diethyl-N'-hydroxyethylethylenediamine to yield the corresponding amidoamine. The reaction conditions selected depend on the nature of

but generally they are in keeping with a simple displacement reaction, that is, the solvent, if utilized, and temperatures are chosen to facilitate the removal of HZ. Thus, the reaction of the fatty acid with the diamine is carried out at a temperature above about 105° C. to have efficient removal of the water that is formed. If

is an acid chloride, a relatively non-polar solvent and a lower temperature are appropriate, along with sufficient means of removing the hydrochloric acid that is formed.

Quaternization of two moles of the amidoamine with a bifunctional compound, X—Y—X, is best carried out at temperatures of from about 40° C. to about 150° C. while utilizing either no solvent or a polar solvent such as water, alcohols or the like.

Representative novel bisquaternary ammonium compounds include the following:

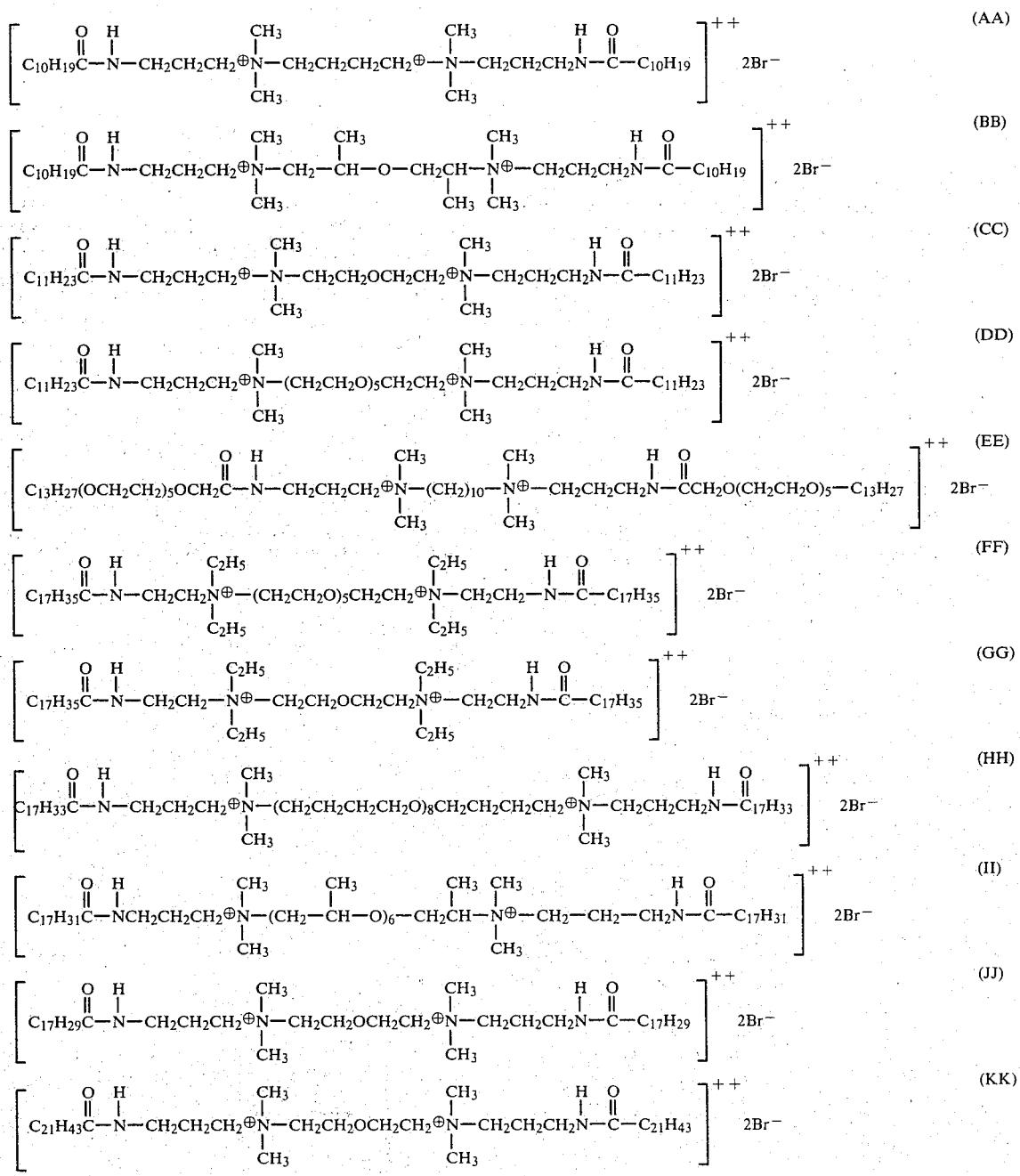

-continued

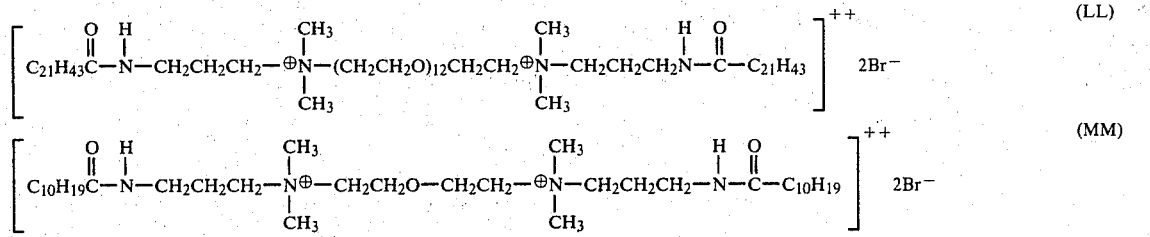

The novel bisquaternary ammonium compounds of the present invention are useful in hair care compositions such as shampoos and conditioning rinses. When utilized in such formulations they provide improved wet and dry combing, reduction in hair fly-away and improved detangling as well as a desirable luster to the hair.

These compounds also exhibit an eye irritancy reducing potential when utilized in compositions also containing other surfactants which are known to exhibit eye irritancy characteristics.

Still further, the compounds of the present invention have been found to exhibit antimicrobial activity against a broad range of organisms, such as gram positive bacteria, gram negative bacteria, fungi and yeast.

The compounds of this invention can be utilized from about 0.1% to about 6.0% by weight of the composition depending on the composition in which they are utilized. If amounts greater than about 6.0% are utilized the resulting compositions could develop formulation problems and such usage would be uneconomical.

Specific embodiments of the present invention are illustrated by the following examples. It will be understood, however, that the present invention is not confined to the specific limitations set forth in the individual examples, but rather to the scope of the appended claims.

EXAMPLE I 50 g (0.49 mole) of 3-dimethylaminopropylamine and 500 ml of methylene chloride are combined in a 1 l. round bottom flask equipped with a reflux condenser, addition funnel and a magnetic stirrer/heating mantle. 100 g (0.49 moles) of 10-undecenoyl chloride are added via a dropping funnel at a rate to insure that the reaction mixture remains below the boiling point. Following the addition of the 10-undecenoyl chloride, the reaction mixture is gradually heated and is allowed to reflux for a period of about 24 hours. After termination of the reaction and appropriate workup, an oily product is obtained which is the desired amidoamine.

67 g (0.25 mole) of the undecenylamidopropyl dimethylamine and 27 g (0.125 mole) of commercially available 1,4-dibromobutane in 500 ml methanol are refluxed until 0.25 moles of bromide ion has been released as estimated by an argentimetric titration.

After recrystallization and analysis the compound is found to be N,N'-undecenylamidopropyl-N,N,N',N'-tetramethyl-1,-4-butylene diammonium bromide having the formula:

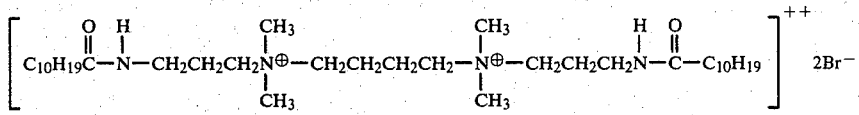

EXAMPLE II 134.2 g (1 mole) of dipropylene glycol is placed in 1 l. 4-neck round bottomed flask equipped with overhead stirrer, dropping funnel, condenser and thermometer. The dipropylene glycol is heated to 80° C. and 270.67 g (1 mole) of phosphorous tribromide (50% excess) are added while stirring rapidly. During the addition of the phosphorous tribromide, the temperature is kept at 80°-85° C. The reaction mixture is stirred for an additional hour, poured into approximately 3 l. of water and neutralized to pH 5.5 with sodium hydroxide while stirring vigorously. After separation of the two layers, the resulting product is collected, dried over anhydrous magnesium sulfate and filtered.

32.5 g (0.125 mole) of the dibromodipropyl ether formed above and 67 g (0.25 mole) undecenylamidopropyl dimethyl amine are combined in 500 ml methanol and refluxed until 0.25 moles of bromide ion are liberated.

After recrystallization from acetone and analysis the compound is found to be N,N'-di(undecenylamidopropyl)-N,N,N',N'-tetramethyl-1,5(2,4-dimethyl-3-oxapentylene)-diammonium bromide having the formula:

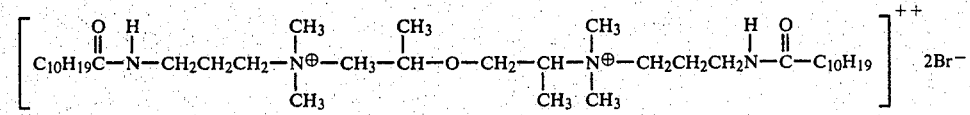

EXAMPLE III 200.32 g (1 mole) lauric acid, 102.04 g (1 mole) 3-dimethyl aminopropylamine and 1 l. toluene are combined in a 2 l. round bottomed flask equipped with a condenser, overhead stirrer and thermometer. The reaction mixture is heated to reflux and the 1 mole of water formed during the reaction is removed via a Dean-Stark trap inserted between the flask and condenser. After removal of the solvent the lauramidopropyl dimethylamine is isolated.

120.2 g (0.4 mole) of the lauramidopropyl dimethylamine and 46.4 (0.2 mole) of β,β'-dibromodiethyl ether are dissolved in sufficient methanol to make a total volume of 1000 ml. This mixture is refluxed in a 2 l. round bottom flask for 72 hours after which 0.4 moles of bromide ion are liberated. After virtually all the methanol has been removed, addition of acetone provides a gradual precipitate of compound CC, N,N'-di(-lauramidopropyl)-N,-N,N',N'-tetramethyl-1,5(3-oxapentylene) diammonium bromide which can be isolated by suction filtration and vacuum drying and is of the formula:

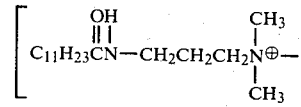

EXAMPLE IV 800 g (~2 moles) of Carbowax 400 (polyethyleneglycol, Union Carbide) are placed in a 2 l. 4-neck round bottomed flask equipped with overhead stirrer, dropping funnel, condenser and thermometer. The material is warmed to 80° C. and 541.4 g (2 moles) of phosphorous tribromide (50% excess) are added while stirring rapidly. During the addition of phosphorous tribromide and one hour following the addition the temperature is kept at 80°-85° C. The reaction mixture is then poured into approximately 4 l. of water and neutralized while stirring vigorously. After separation of the two layers the product is collected, dried over anhydrous magnesium sulfate and filtered.

To obtain starting materials with better than 95% of a given homologue multiple passes through a falling film molecular still, as marketed by Kontes Glass Co., can be employed. Gas chromatographic analysis utilizing a flame ionization detector can be used to monitor the distillation.

120.2 g (0.4 mole) of lauramidopropyl dimethylamine and 66.82 g (0.2 mole) of 1,12 dibromoheptaethyleneglycol are refluxed in methanol for 96 hours to yield compound DD, N,N'-di(lauramidopropyl)-N,N,N',N'-tetramethyl-1,12(3,6,-9,12,15 pentaoxadodecylene) diammonium bromide of the formula:

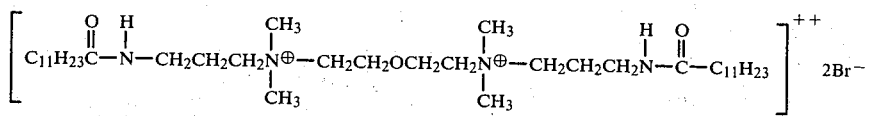

EXAMPLE V 95.73 g (0.2 mole) of tridecyl (penta-1-oxapropene) oxaethane carboxylic acid, $C_{13}H_{27}(O\ CH_2CH_2)_5$-$OCH_2C$—$OOH$, and 20.4 g (0.2 mole) of 3-dimethylaminopropylamine are heated in toluene to effect amide formation. The amidoamine is then refluxed with 30.1 g (0.1 mole) of 1,10-dibromodecane in methanol to yield compound EE, N,N'di(tridecyl(penta-oxapropene) oxaethanecarboxamidopropyl-N,N,N',N'-tetramethyl-1,10 decylene) diammonium dibromide of the formula:

[
CH₃CH—C₁₀H₂₀—(OCH₂CH₂)₅OCH₂CN—CH₂CH₂CH₂N⊕—(CH₂)₁₀—N⊕—CH₂CH₂CH₂
    |                              ‖   |                |              |
    CH₃                            O   H                CH₃            CH₃

NC—CH₂O(CH₂CH₂O)₅—C₁₀H₂₀—CH—CH₃
‖                              |
O                              CH₃
|
H
]²⁺ 2Br⁻

EXAMPLE VI 142.24 (0.5 mole) stearic acid and 58.09 g (0.5 mole) 2-diethylaminoethylamine are heated in toluene to produce 0.5 mole stearamidoethyl diethylamine. 76.53 g (0.2 mole) of the stearamidoethyl diethylamine are then reacted with 49.60 g (0.1 mole) 1,12-dibromoheptaethylene glycol to yield compound FF, N,N'di(stearamidoethyl)-N,N,N',N'-tetraethyl-1,12(3,6,9,12,15-pentaoxadodecylene)diammonium dibromide of the formula:

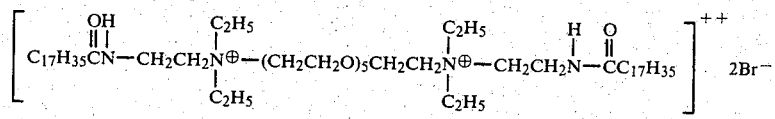

EXAMPLE VII

Utilizing the equipment described in Example I, 76.53 g (0.2 mole) of stearamidoethyl diethylamine are quaternized with 23.2 g of β,β'-dibromodiethyl ether to yield bisquaternary ammonium compound GG, N,N'-di(-stearamidoethyl)-N,N,N',N'-tetraethyl-1,5(3-oxapentylene)diammonium dibromide of the formula:

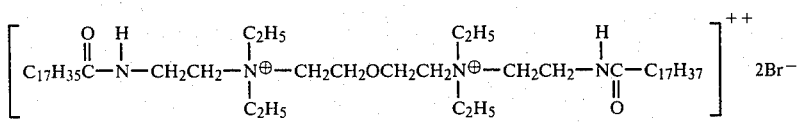

EXAMPLE VIII

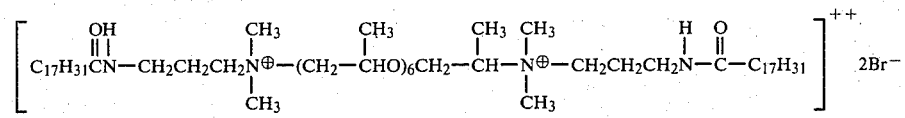

650 g (1 mole) of polybutyleneglycol (Teracol 650, DuPont) is heated to 80° C. in a 4-neck glass reactor equipped with an overhead stirrer, reflux condenser, addition funnel and thermometer. 270.67 g (1 mole) phosphorous tribromide (50% excess) are added while stirring vigorously. During the addition of the phosphorous tribromide, the temperature is maintained between 80° C. and 85° C. The reaction mixture is stirred for an additional hour, poured into 3 l. of water and neutralized to pH 5.5 with sodium hydroxide while stirring rapidly. After separation of the two layers the product is collected, dried over anhydrous magnesium sulfate and filtered.

77.6 g (0.1 mole) of the above dibromopolybutylene glycol and 76.53 g (0.2 mole) of stearamidoethyl diethylamine were dissolved in 500 ml ethanol and refluxed for 96 hours to yield compound HH, N,N'-di(oleoamidoethyl)-N,N,N',N'-tetraethyl-1,44(5,10,15,20,25,30,35,40-octaoxatetratetracontylene)diammonium dibromide of the formula:

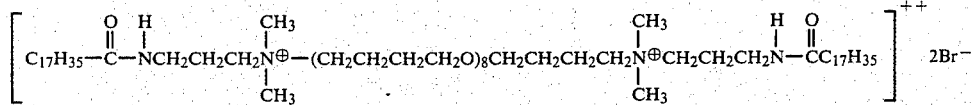

EXAMPLE IX 280.45 g (1 mole) linoleic acid and 102.0 g (1 mole) 3-dimethyl aminopropylamine are dissolved in 1.2 l. toluene and refluxed in a reaction apparatus equipped with a reflux condenser and a Dean-Stark trap. After 1 mole of water has been removed, the toluene is removed by flash evaporation. The bisquaternary ammonium compound is then prepared by heating the above amidoamine with the dibromo derivative of polypropylene glycol 425 which can be prepared using a method analogous to that utilized in Example IV. The resulting bisquaternary ammonium compound II is N,N'-di(octadidecenamidopropyl)-N,N,N',N'-tetramethyl-1,20 (2,5,8,11,14,17,20-heptamethyl-3,6-9,12,15,18-hexaoxaeicosylene) diammonium dibromide of the formula:

EXAMPLE X 69.6 g (0.25 mole) linolenic acid and 25.5 g (0.25 mole) 3-dimethyl aminopropylamine are dissolved in 500 ml. xylene and heated at reflux until 0.25 mole of water (4.5 g) have been removed. After removal of the xylene, the amidoamine is analyzed using spectroscopic and titrimetric analysis methods. 72.2 g (0.2 mole) of the linolenamidopropyl dimethylamine and 23.2 g (0.1 mole) of β,β'-dibromodiethyl ether are dissolved in methanol to yield a 750 ml. solution. This mixture is refluxed in a round bottom flask equipped with reflux condenser and the progress of the reaction is estimated by argentometric titration of the bromide liberated. After recrystallization from acetone, compound JJ can be obtained in approximately a 96.7% yield. The N,N'-di(octatridecenamidopropyl)-N,N,N',N'-tetramethyl-1,5(3-oxapentylene)-diammonium dibromide is of the formula:

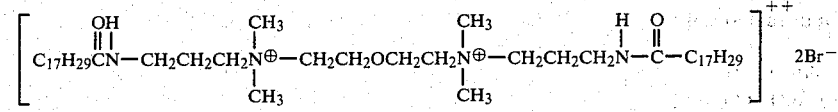

EXAMPLE XI 340.2 g (2 moles) of docosanoic acid and 204 g (2 moles) of 3 dimethylaminopropylamine are dissolved in 2 l. toluene while heating to reflux. After refluxing for several hours, 36 g of water (2 moles) are removed utilizing a Dean-Stark trap arrangement.

After removal of the toluene, 212.7 g (0.5 mole) of the resulting docosamidopropyldimethylamine are quaternized with 58 g (0.25 mole) of β,β'-dibromodiethyl ether to yield, after recrystallization, compound KK, N,N'-di(docosamidopropyl)-N,N,N',N'-tetramethyl-1,5(3-oxapentylene)diammonium dibromide of the formula:

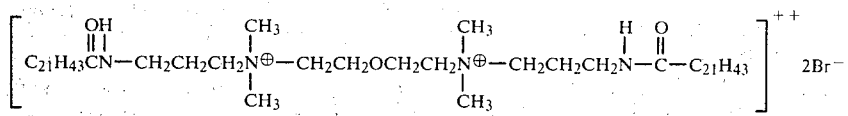

EXAMPLE XII 212.7 g (0.5 mole) of the docosamidopropyldimethylamine prepared in Example XI and 179.0 g (0.25 mole) 1,38 dibromo(3,6,9,12,15,18,21,24,27,30,33,36 dodecaoxaoctatricontane) which can be prepared and purified according to the method described in Example IV, are dissolved in sufficient ethanol to make a two liter solution. The reaction mixture is refluxed until 0.5 mole of bromide ion has been liberated and the solvent is subsequently removed by vacuum evaporation. A semi-solid is obtained which can be identified as compound LL, N,N'-di(docosamidopropyl)-N,N,N',N'-tetramethyl-1,38(3,6,9,12,15,18,21,24,-27,30,33,36-dodecaoxaoctatricontylene)diammonium dibromide of the formula:

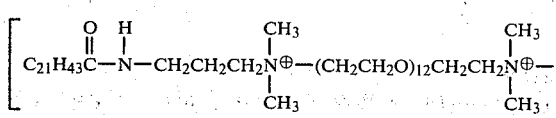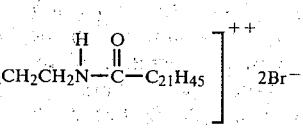

EXAMPLE XIII

To test the hair fly-away characteristics of the novel bisquaternary ammonium compounds of the present invention, the following test procedure can be utilized.

The hair to be utilized is formed into six inch long, 1.5 gram weight tresses, cleaned with methanol first, then with a 1% solution of sodium lauryl sulfate followed by a rinse with distilled water. The tress is then dried in an oven at 55° C. The tresses except for the controls are then treated with the test compounds and redried at 55° C.

An electrometer (Electrometer Model 610C, Keithley Instrument Co., Cleveland, Ohio) to serve as a coulomb meter for direct measurement of charge is attached to a Faraday pail and switched on.

The test tresses are singly taken out of the drying oven, held at the tied end and brushed or combed twenty strokes alternating between front and back side of the tress as held by the operator. A clean brush or comb is utilized and the velocity with which the brush or comb is traversed through the tress is maintained constant as much as possible. Further, since the electrostatic charges are capable of being quickly dissipated into the atmosphere, the procedure consists of uniformly brushing or combing 20 strokes in a period of 10 seconds and immediately following the last stroke, the lid of the Faraday cage is opened and the tress is dropped into the Faraday pail without contacting any other object and the lid is replaced. The charge in coulombs is read from the electrometer and the tress is then removed from the Faraday pail and the instrument is reset for the next tress sample.

One percent aqueous solutions of compounds CC, JJ and LL were prepared and when tested against a control in accordance with the above procedure each of these compounds exhibited a charge reduction of greater than 95% when compared to the control. Since electrostatic charge buildup creates fly-away in atmospheres of low humidity, these compounds are useful to prevent said fly-away condition.

EXAMPLE XIV-XVII

The bisquaternary ammonium compounds of the present invention can be tested for ocular irritation by the following modified Draize Test (J. H. Draize et al., Toilet Goods Assn. No. 17, May 1952, No. 1, Proc. Sci. Sect.).

An 0.1 ml. sample of a neutral composition under test is dropped into one eye of an albino rabbit, the other eye serving as a control. Six rabbits are employed for each composition. Observations are made after 1, 24, 48, 72 and 96 hours and 7 days after initial instillation; second and third instillations are made after the 24 and 48 hour readings. Results may vary from substantially no change or only a slight irritation in the appearance of the rabbit's eye after 7 days to severe irritation and/or complete corneal opacity. Ocular lesions are scored for the cornea, iris and conjunctiva with a higher number indicating greater ocular irritation and the scores are added to give a total numerical value for each reading for six rabbits and averaged. The averaged score is an indication of the irritation potential of the composition under test. Based on the averaged score, descriptive irritation evaluation may be given, e.g., none, slight, moderate, severe, as the case may be.

A shampoo composition is prepared consisting of the following ingredients:

|  | % w/w |
|---|---|
| Cocoamido sulfobetaine | 8.00 |
| Sodium tridecylether (4.2) sulfate | 6.00 |
| Polyethylene glycol 150 distearate | 1.50 |
| Propylene glycol | 1.00 |
| HCl (15%) | 1.00 |
| Distilled water | 82.50 |

This formulation serves as a control with three additional formulations being made with the only difference being that in each of said formulations 3.50% of distilled water is replaced with 3.50% of compound JJ, KK and LL respectively. These formulations are then tested in accordance with the above procedure and the results are shown below in Table I.

TABLE I

| EXAMPLE | FORMULATION | RATING |
|---|---|---|
| XIV | Control | Severe Irritant |
| XV | JJ | Slight Irritant |
| XVI | KK | Slight-Moderate Irritant |
| XVII | LL | Slight-Moderate Irritant |

EXAMPLE XVIII

In order to demonstrate the antimicrobial properties of the novel compounds of the present invention, the following standard Minimum Inhibiting Concentration test can be performed to determine the lowest effective concentration of the novel compounds that will inhibit the growth of various test organisms. First, 200 mg. each of the compounds, AA, CC, GG, II and MM are placed in 100 ml. of a 10% ethyl alcohol solution resulting in a concentration of 2.00 mg/ml. and then 11 serial two fold dilutions are made to a final concentration of 0.0001 mg/ml. Thus, a range of concentrations of from 0.0001 mg/ml. to 2.00 mg/ml. are prepared. Separately, 1000 ml. of a standard Antibiotic Medium #3 is innoculated with 1 ml. of a 24 hour broth culture of each of the test organisms and the resulting solutions are dispersed in 2 ml. portions into 13 mm × 100 mm test tubes at 4° C. Two test tubes for each of the test organisms are prepared.

Then, 0.4 ml. of each concentration of the compound to be tested is placed in each of the test tubes, which are then shaken and placed at a temperature of 35° C. for a period of 18 hours for bacteria, 25° C. for a period of 3 days for yeast, and 25° C. for a period of 1 month for fungi. The end point of the activity is determined by streaking utilizing a calibrated loop to Trypticase Soy Agar to determine the last tube (concentration) with growth and the next greatest concentration. The results are shown below in Table II:

TABLE II

| TEST ORGANISM | MINIMUM INHIBITING CONCENTRATION mg/ml COMPOUND | | | | |
|---|---|---|---|---|---|
| | AA | CC | GG | II | MM |
| Staphylococcus aureos | 0.125 | 0.250 | 0.625 | 2.000 | 2.000 |
| Staphylococcus epidermis | 0.0625 | 0.125 | 0.0625 | 1.000 | 1.000 |
| Staphylococcus pyogenes | 0.500 | 0.250 | <2.000 | <2.000 | 0.500 |
| Pseudomonas aeruginosa | 1.00 | 0.250 | <2.000 | 2.000 | 1.000 |
| Proteus mirabilis | <2.000 | <2.000 | <2.000 | <2.000 | <2.000 |
| Proteus vulgaris | 0.250 | <2.000 | <2.000 | <2.000 | 0.250 |
| Escherichia coli | 0.125 | 0.125 | 1.000 | 0.500 | 0.125 |
| Candida albicans | 0.250 | 0.063 | 0.031 | 0.250 | 0.063 |
| Aspergillus niger | 0.250 | 0.125 | 0.250 | 0.500 | 0.125 |
| Epidermophyton flocossum | 0.125 | 0.0625 | 0.250 | 0.500 | 0.250 |
| Trichophyton mentagrophytes | 0.016 | 0.016 | 0.016 | 0.031 | 0.016 |

These results, when compared to a control bacteriostatic and/or bacteriocidal agent such as cetyl pyridinium chloride, showed that the novel compounds of the present invention exhibit bacteriostatic and bacteriocidal properties at relatively low concentrations and would be good antimicrobial agents with the exception against the strain of Proteus mirabilis utilized. Proteus mirabilis is known to be resistant to common antimicrobial agents and the results are therefore not unexpected.

While the present invention has been described and illustrated with reference to certain preferred embodiments thereof, those skilled in the art will appreciate that various modifications, changes, omissions and substitutions can be made without departing from the spirit of the invention. It is intended, therefore, that the invention be limited only by the scope of the appended claims.

We claim:

1. A compound of the formula

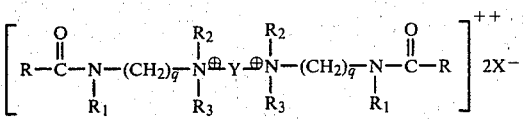

wherein

R is straight or branched chain alkyl, alkenyl, or alkaryl containing from about 8 to 30 carbon atoms and may be optionally interrupted by oxyalkylene groups containing up to a total of 20 carbon atoms;

$R_1$ is hydrogen or alkyl, alkaryl or hydroxyalkyl of from about 1 to 10 carbon atoms;

$R_2$ and $R_3$ are the same or different and are alkyl of from 1 to 6 carbon atoms, hydroxyalkyl of from 1 to 4 carbon atoms or alkaryl of from 1 to 10 carbon atoms;

q is an integer from 2 to 6;

Y is oxyalkylene of the formula

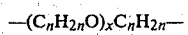

wherein n is an integer from 2 to 4 and x is an integer from 1 to 16; and

X is an anion.

2. A compound according to claim 1 wherein R is straight or branched chain alkyl containing from about 8 to 30 carbon atoms.

3. A compound according to claim 1 of formula

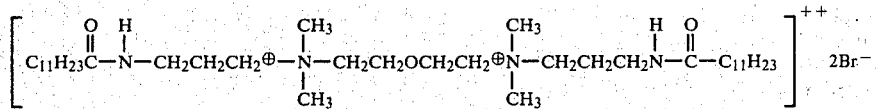

4. A compound according to claim 1 of formula

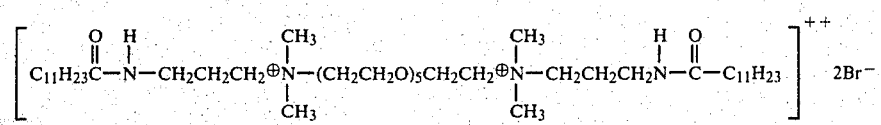

5. A compound according to claim 1 of formula

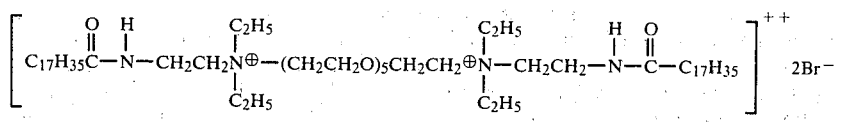
6. A compound according to claim 1 of formula
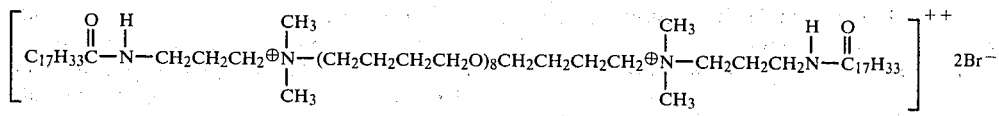
7. A compound according to claim 1 of formula
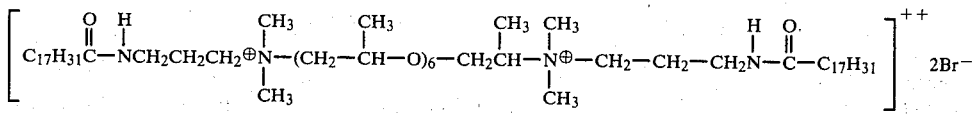
8. A compound according to claim 1 of formula
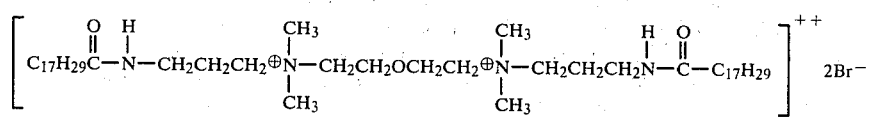
* * * * *